United States Patent [19]

Naegeli

[11] 3,943,073

[45] Mar. 9, 1976

[54] ODORANT COMPOSITIONS CONTAINING HYDROZOLENONES

[75] Inventor: Peter Naegeli, Wettingen, Switzerland

[73] Assignee: Givaudan Corporation, Clifton, N.J.

[22] Filed: Feb. 24, 1975

[21] Appl. No.: 552,521

Related U.S. Application Data

[62] Division of Ser. No. 413,469, Nov. 7, 1973.

[30] Foreign Application Priority Data

Nov. 15, 1972 Switzerland ...................... 16607/72

[52] U.S. Cl. ............................ 252/522; 260/586 F

[51] Int. Cl.$^2$ ........................ A61K 2/46; C11B 9/00

[58] Field of Search .................................. 252/522

[56] References Cited

OTHER PUBLICATIONS

Kratcho et al.: Tetrahedron 26, 5437–5446 (1970).

DeBrossia et al.: J. C. S. Chem. Comm. 1972, p. 855.

DeBroissia et al.: Bull. Chem. Soc. France, No. 11, 4314–4318 (1972).

*Primary Examiner*—Herbert Levine

*Assistant Examiner*—G. E. Schmitkons

*Attorney, Agent, or Firm*—Thomas Cifelli, Jr.

[57] ABSTRACT

Novel hydroazulenones, a process for making them and odorant compositions containing the novel compounds are disclosed.

4 Claims, No Drawings

ODORANT COMPOSITIONS CONTAINING HYDROZOLENONES

This is a division of application Ser. No. 413,469, filed Nov. 7, 1973.

FIELD OF THE INVENTION

This invention relates to the fields of new chemicals and odorant compositions.

SUMMARY OF THE INVENTION

The hydroazulenones provided by the present invention have the following general formula

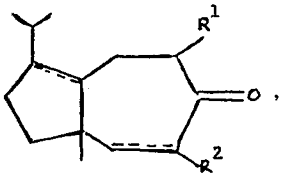

(I)

wherein $R^1$ and $R^2$ each independently represent a hydrogen atom or a lower alkyl group and one of the two broken lines represents an additional bond.

Examples of hydroazulenones falling within formula I are 1-isopropyl-3a-methyl-1,2,3,3a,6,7,8,8a octahydroazulen-6-one and 1-isopropyl-3a-methyl-2,3,3a,4,5,6,7,8,-octahydroazulen-6--one.

The term "lower alkyl" as used in this description and in the accompanying claims means straight-chain and branched-chain groups containing 1-6 carbon atoms (e.g. methyl, ethyl, propyl, isopropyl and tertbutyl). A preferred lower alkyl group is the methyl group.

According to the process provided by this invention, the hydroazulenones of formula I are manufactured by cyclising a cyclopentene derivative of the general formula

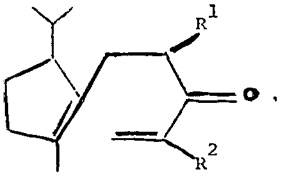

(II)

wherein $R^1$ and $R^2$ have the significance given earlier, in an organic solvent in the presence of a Lewis acid.

DESCRIPTION OF THE PREFERRED EMBODIMENTS

Suitable Lewis acids which can be used are the usual halides, preferably tin tetrachloride and titanium tetrachloride. Examples of inert organic solvents in which the cyclisation can be carried out are dioxane, diethyl ether, benzene, toluene and nitromethane. Depending on the solvent, the cyclisation can be carried out within a wide temperature range between −40°C and the reflux temperature of the mixture, preferably between 0°C and room temperature.

The working up of the cyclisation mixture and the isolation and purification of the hydroazulenones of formula I can be carried out according to known methods. The purification is preferably carried out by chromatography on silica gel, but it can also be carried out by distillation.

The cyclopentene derivatives of formula II can be prepared by oxidizing a compound of the general formula

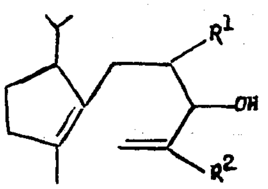

(III)

wherein $R^1$ and $R^2$ have the significance given earlier.

The oxidation can be carried out in a manner known per se according to methods which are generally known for the oxidation of allylic hydroxy groups. Examples of oxidising agents which can be used are chromic acid (in its various forms such as, for example, Jones reagent), activated manganese dioxide, $SO_3$ (preferably as the pyridine complex in the presence of dimethyl sulphoxide and triethylamine), silver oxide or silver carbonate in the presence of diatomaceous earth. The working up of the oxidation mixture as well as the purification of the hydroazulenones of formula I can be carried out according to customary methods.

The compounds of formula III can be prepared in a manner known per se from a compound of the general formula

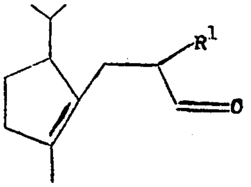

(IV)

wherein $R^1$ has the significance given earlier, by reaction with an organometallic compound, especially with an alkali metal acetylide or with a Grignard compound of the general formula

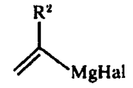

wherein $R^2$ has the significance given earlier and Hal represents a chlorine or bromine atom.

When a compound of formula IV is reacted with an acetylide it is necessary to catalytically partially hydrogenate the initially obtained compound of the general formula

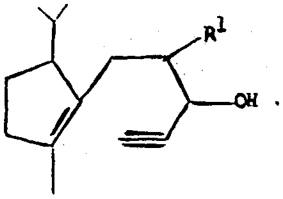

(V)

wherein $R^1$ has the significance given earlier, in a manner known per se; for example, in the presence of a Lindlar catalyst ($Pd/CaCO_3$ deactivated with PbO).

Insofar as they are not known, the compounds of formula IV can be prepared, for example, by reacting 3-isopropenyl-1-methyl-2-methylene-cyclopentan-1-ol with a vinyl ether of the general formula

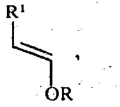

(VI)

wherein $R^1$ has the significance given earlier and R represents an alkyl group, and hydrogenating a resulting 3-isopropenyl-cyclopentene of the general formula

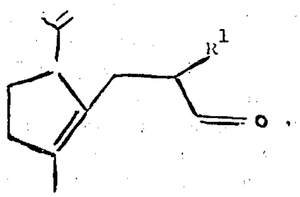

(VII)

wherein $R^1$ has the significance given earlier, in a known manner to give the corresponding 3-isopropyl compound.

The hydroazulenones of formula I possess particular fragrance properties, especially in the foreground is a woody basic note. They can accordingly be used as odorants in perfumery; for example, in the manufacture or for the modification of the fragrance of odorant compositions such as perfumes, perfume bases, etc. by addition of olfactory perceptible amounts (e.g. 0.1–10 wt %) to mixtures of known odorants. The hydroazulenones can be used alone or in the form of odorant compositions for the perfuming of technical and cosmetic products of all types; for example, of solid and liquid detergents, synthetic washing agents, aerosols, soaps, creams, lotions, etc. in concentrations of, for example, about 0.001–0.1 %. They can also be used as starting materials for the manufacture of other odorants.

The following Examples illustrate the process provided by the present invention:

EXAMPLE 1

A solution of 1.24 g of 3-isopropyl-1-methyl-2-(3-oxo-4-pentenyl)-1-cyclopentene in 60 ml of absolute benzene and 15 ml of absolute ether was treated with 18 ml of a 0.5-M benzene solution of tin tetrachloride with vigorous stirring at 0°C during 30 minutes. The mixture was stirred for a further 30 minutes at 0°C and for 1.5 hours at room temperature and then poured into an ice-cold 2-N soda solution covered with ether. By thorough extraction with ether and working up of the extract in the usual manner, there were obtained 1.1 g of an oily crude product which, after distillation under reduced pressure, yielded 0.5 g of 1-isopropyl-3a-methyl-1,2,3,3a,6,7,8,8a-octahydroazulen-6-one (mixture of two isomers); $b.p._{0.005}$ = 80°C;

UV (cyclohexane): $\lambda_{max} = 228$ nm ($\epsilon = 9400$);

IR (film):$\nu$ = 1680, 1615, 1470/50, 1420, 1390/80/70, 1260, 1230, 1180, 1150, 1130, 1110, 900, 850 and 770/60 $cm^{-1}$.

The compound has a woody, earthy, patchouli odour.

The starting material was prepared as follows:

A solution of 2.1 g of 2-(3-hydroxy-4-pentenyl)-3-isopropyl-1-methyl-1-cyclopentene in 100 ml of acetone was treated with 4 ml of Jones reagent at −10°C. After 2 minutes, the solution was poured into an ice-cold 2-N soda solution and the mixture extracted with ether. The extract was worked up in the usual manner and yielded 2 g of a yellowish oil which, after distillation under reduced pressure, gave 1.6 g of pure 3-isopropyl-1-methyl-2-(3-oxo-4-pentenyl)-1-cyclopentene; $b.p._{0.01}$ = 65°C;

IR (film):$\nu$ = 1700/1685, 1620, 1470, 1402, 1385, 1365, 1185, 1100, 990, 965 $cm^{-1}$.

EXAMPLE 2

A solution of 1.3 g of 3-isopropyl-1-methyl-2-(4-methyl-3-oxo-4-pentenyl)-1-cyclopentene in 40 ml of absolute nitromethane and 8 ml of absolute ether was treated at −25°C with 13.5 ml of a 0.5-M solution of tin tetrachloride in nitromethane. After stirring for 1.5 hours at −15°C, the mixture was poured into an excess of cold soda solution and worked up in the usual manner. The oily crude product was distilled under reduced pressure, there being obtained a 1:1 mixture of 1-isopropyl-3a,5-dimethyl-1,2,3,3a,6,7,8,8a-octahydroazulen-6-one (Component A) and 1-isopropyl-3a,5-dimethyl-2,3,3a,4,5,6,7,8-octahydroazulen-6-one (Component B); $b.p._{0.005}$ = 80°C. The mixture could be separated into the individual components by chromatography on silica gel.

Component A (of isomer mixture):

UV (cyclohexane):$\lambda_{max} = 239$ nm ($\epsilon = 9000$);

IR (film):$\nu$ = 1675, 1640, 1470/50, 1380/70, 1190, 1095, 1040, 920 and 900 $cm^{-1}$.

Odour: camphoraceous, woody, cedar-like, sweet honey nots,

Component B (of isomer mixture):

IR (film)$\nu$ = 1710, 1460, 1375/60, 1335/05, 1205, 1150, 1130, 1110, 1100, 1075, 1025, 990, 970, 940, 920, 900, 860 and 810 $cm^{-1}$.

Odour: woody flowery, slightly camphoraceous, tobacco-like.

The starting material was prepared in a manner analogous to that described in Example 1 from 2-(3-hydroxy-4-methyl-4-pentenyl)-3-isopropyl-1-methyl-1-cyclopentene; $b.p._{0.01}$ = 80°C;

UV (cyclohexane):$\lambda_{max} = 214$ nm ($\epsilon = 9000$);

IR (film):$\nu$ = 1680, 1635, 1465/55, 1385, 1365, 1090, 935 $cm^{-1}$.

The following Example illustrates an odorant composition containing a hydroazulenone provided by the present invention:

EXAMPLE A

Odorant composition containing 1-isopropyl-3a-methyl-1,2,3,3a,6,7,8,8a-octahydroazulen-6-one.

| | Parts by weight |
|---|---|
| Phenylethyl alcohol | 200 |
| Citronellol | 100 |
| Geraniol | 75 |
| α-Ionone | 25 |
| Phenylethyl acetate | 15 |
| Linalool | 50 |
| Hydroxycitronellal | 25 |
| Benzyl acetate | 10 |
| Rosewood oil Brazilian | 25 |
| Geranium oil | 25 |
| Cinnamic alcohol | 30 |
| Bergamot oil | 70 |
| Lavender oil Mt. Blanc | 250 |
| 1-Isopropyl-3a-methyl-1,2,3,3a,6,7,8,8a-octahydroazulen-6-one | 100 |
| | 1000 |

By the addition of the hydroazulenone, the composition has a fuller and more vivid effect. The background odour is somewhat reminiscent of withered rose-blossoms.

What we claim is:

1. An odorant composition which contains as an essential odor-imparting ingredient an hydroazulenone having the formula:

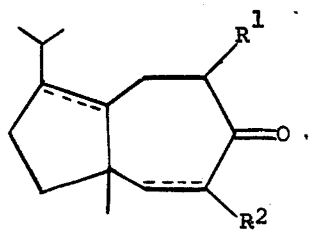

(I)

wherein $R^1$ and $R^2$ each independently represent a hydrogen atom or a lower alkyl group and one of the two broken lines represents an additional bond.

2. An odorant compositions which contains as an essential odor-imparting ingredient an hydroazulenone having the formula: 1-isopropyl-3a-methyl-1,2,3,3a,6,7,8,8a-octahydroazulen-6-one.

3. An odorant composition which contains as an essential odor-imparting ingredient an hydroazulenone having the formula: 1-isopropyl-3a,5-dimethyl-1,2,3,3a,6,7,8,8a-octahydroazulen-6-one.

4. An odorant composition which contains as an essential odor-imparting ingredient an hydroazulenone having the formula: 1-isopropyl-3a,5-dimethyl-2,3,3a,4,5,6,7,8-octahydroazulen-6-one.

* * * * *